Feb. 10, 1953 E. S. BOERNER Plant Pat. 1,165
CHRYSANTHEMUM PLANT
Filed April 21, 1952
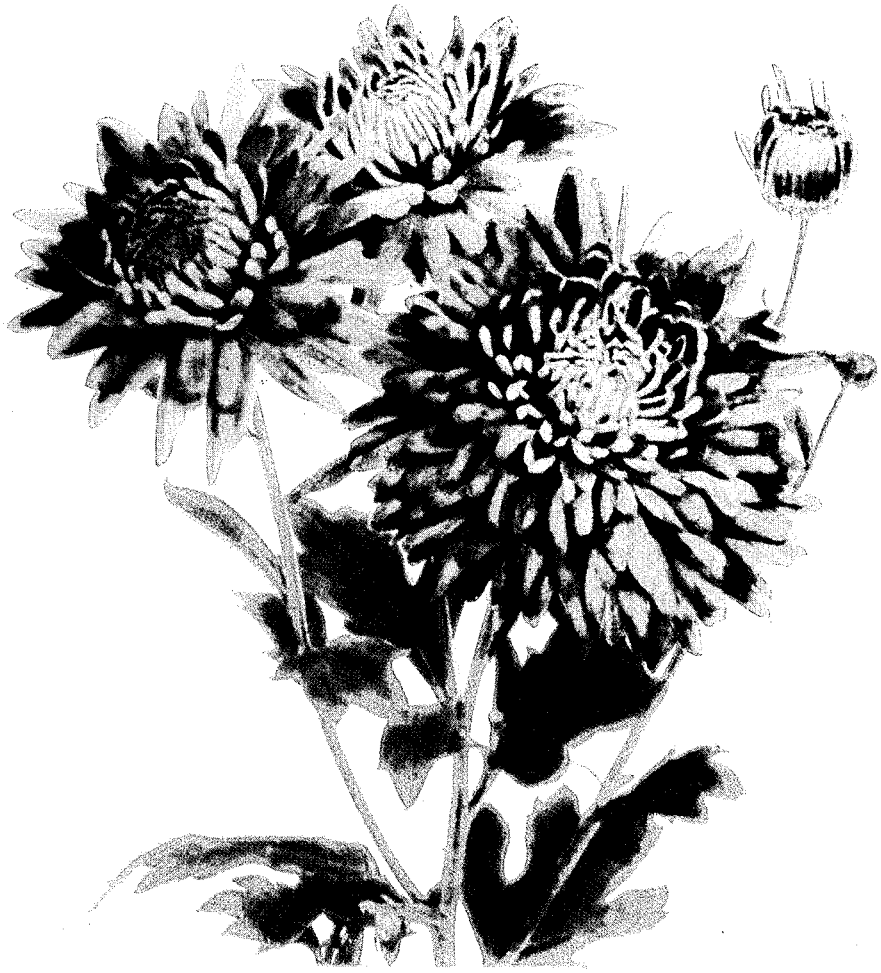
Inventor.
E. S. Boerner
By: Robert Cobb
Attorneys.

Patented Feb. 10, 1953

Plant Pat. 1,165

UNITED STATES PATENT OFFICE 1,165

CHRYSANTHEMUM PLANT

Eugene S. Boerner, Newark, N. Y., assignor to Jackson & Perkins Company, Newark, N. Y., a corporation of New York Application April 21, 1952, Serial No. 283,375

1 Claim. (Cl. 47—60)

The present invention relates to a new and distinct variety of chrysanthemum plant that was originated by me by crossing the variety "Courageous" (unpatented) with an unnamed and unpatented variety known as 4408-4 Indiana Seedling.

The primary objective of this cross was to produce a large-flowered, early-blooming red chrysanthemum. This objective was fully achieved, as evidenced by the fact that the blooms of my new variety are larger than any hardy reds known to date, and are almost a pure red color, with only a slight yellow reverse in the bud. The blooming period of my new variety usually begins about September 5th, which is quite early in the case of red chrysanthemums.

More specifically speaking, my new variety is distinguished from its parents, as well as from all other varieties, by the following unique combination of outstanding characteristics:

(1) Its early blooming habit;

(2) The large size of the flowers; and (3) The distinctive color of the flowers which in general tonality are characterized as Nopal Red.

Asexual reproduction of my new variety by both top cuttings and by underground runners, at Newark, New York, shows that the foregoing characteristics come true to form and are established and transmitted through succeeding propagations.

The accompanying drawing shows typical specimens of the new variety, with the flowers and foliage in different stages of development.

The following is a detailed description of the new variety, as observed in the fields at Newark, New York, in the latter part of the month of September and in the latter part of the morning, with color terminology in accordance with Ridgway's Color Standards and Nomenclature:

Parentage: "Courageous" × 4408-4 Indiana Seedling.

Classification: Decorative; large; very double.

Growth: Upright; strong; attains a height of from 2½ feet to 3 feet.

Cold resistance: Winter hardy, frost-resistant flowers, as determined by comparison with other varieties grown under comparable conditions.

Blooming habit: In Newark, New York, climatic area, date of start of bloom is about September 5th, and the plant is very free blooming until severe freezing in October and November.

Bud:

*Color.*—When sepals first divide—Victoria Lake, Plate 1. When petals begin to unfurl—Oxblood Red, Plate 1. When half blown—inside of petals: Garnet Brown, Plate 1, overcast lightly with Nopal Red, Plate 1; reverse of petals: Pinard Yellow, Plate 4, lightly overcast with Nopal Red, Plate 1.

*Peduncle.*—Color—Light Cress Green, Plate 31. Strength—stiff; erect.

Bloom:

*Size.*—3½ inches to 4 inches.

*Stems.*—Strong; normal.

*Form.*—Decorative.

*Petalage.*—Double.

*Color.*—Center of flower—Nopal Red, Plate 1. Outer petals—Nopal Red, Plate 1, lightly overcast with Garnet Brown, Plate 1. Base of petals—Pale Lemon Yellow, Plate 4. Inside of petals—Carmine, Plate 1, lightly overcast with Nopal Red, Plate 1. Reverse of petals—Nopal Red, Plate 1, with slight indication of Amber Yellow, Plate 16, which disappears quickly.

*Petals.*—Texture—medium. Form—oval.

Fragrance: Characteristic chrysanthemum.

Plant:

*Form.*—Upright; compact.

*Growth.*—Free.

Foliage:

*Size.*—Medium.

*Quantity.*—Normal.

*Color.*—Upper side—Dark Cress Green, Plate 31; reverse side—Cress Green, Plate 31.

*Texture.*—Leathery.

I claim:

A new and distinct variety of chrysanthemum plant of the decorative class, substantially as herein shown and described, characterized particularly as to novelty by the large size of its flowers, by the distinctive Nopal Red general color tonality of its flowers, and by its early-flowering, winter-hardy and frost-resistant habits of growth.

EUGENE S. BOERNER.

No references cited.